(12) United States Patent
Takahashi et al.

(10) Patent No.: US 10,563,242 B2
(45) Date of Patent: Feb. 18, 2020

(54) ENZYME ELECTRODE AND BIOSENSOR USING THE SAME

(71) Applicants: ARKRAY, Inc., Kyoto (JP); Ultizyme International Ltd., Tokyo (JP)

(72) Inventors: Yuka Takahashi, Tokyo (JP); Junko Shimazaki, Tokyo (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 193 days.

(21) Appl. No.: 15/601,151

(22) Filed: May 22, 2017

(65) Prior Publication Data
US 2017/0335363 A1    Nov. 23, 2017

(30) Foreign Application Priority Data
May 23, 2016   (JP) .................................. 2016-102232

(51) Int. Cl.
*G01N 27/327*    (2006.01)
*C12Q 1/00*    (2006.01)
*C12Q 1/54*    (2006.01)

(52) U.S. Cl.
CPC ............. *C12Q 1/002* (2013.01); *C12Q 1/005* (2013.01); *C12Q 1/54* (2013.01); *G01N 27/327* (2013.01); *C12Q 1/00* (2013.01)

(58) Field of Classification Search
CPC ............. G01N 27/327; G01N 27/3272; C12Q 1/002–005
See application file for complete search history.

(56) References Cited

U.S. PATENT DOCUMENTS

| | | | | |
|---|---|---|---|---|
| 5,443,701 A | * | 8/1995 | Willner | C12Q 1/003 204/290.11 |
| 2015/0192537 A1 | * | 7/2015 | Sekimoto | G01N 27/327 204/403.14 |
| 2016/0177365 A1 | * | 6/2016 | Katsuki | G01N 27/3272 205/777.5 |

FOREIGN PATENT DOCUMENTS

| | | | |
|---|---|---|---|
| JP | 2014-006154 A | 1/2014 | |
| WO | WO 2015/020149 A1 * | 2/2015 | ........... G01N 27/327 |

OTHER PUBLICATIONS

Yamaoka et al., "SPCE Based Glucose Sensor Employing Novel Thermostable Glucose Dehydrogenase, FADGDH: Blood Glucose Measurement with 150nL Sample in one Second," Journal of the Diabetes Science and Technology vol. 1, issue 1, Jan. 2007 (Year: 2007).*

Jul. 2013 Wako BioWindow catalog, twenty pages total (Year: 2013).*

(Continued)

*Primary Examiner* — Alexander S Noguerola
(74) *Attorney, Agent, or Firm* — Morgan, Lewis & Bockius LLP (57) ABSTRACT

The disclosure discloses an enzyme electrode comprising; an electrode comprising a current collector; a monolayer-forming molecule bound to the surface of the current collector; and a glucose dehydrogenase comprising a cytochrome C subunit bound to the monolayer-forming molecule; wherein electrons are transferred between the glucose dehydrogenase and the current collector by oxidation-reduction reaction of the glucose dehydrogenase.

14 Claims, 8 Drawing Sheets

(56) References Cited

OTHER PUBLICATIONS

Gamella et al., "Activation of a Biocatalytic Electrode by Removing Glucose Oxidase from the Surface-Application to Signal Triggered Drug Release," Applied Materials & Interfaces, Letter, published Aug. 1, 2014, pp. 13349-13353 plus Supporting Information pp. 1-9. (Year: 2014).*

Freire et al., "Direct Electron Transfer: An Approach for Electrochemical Biosensors with Higher Selectivity and Sensitivity," Journal of the Brazilian Chemical Society, 14: 230-243 (2003).

Extended European Search Report issued in corresponding European Patent Application No. 17172074.1 dated Aug. 31, 2017.

Yamazaki et al., "Construction and characterization of direct electron transfer-type continuous glucose monitoring system employing thermostable glucose dehydrogenase complex," Analytical Letters, 41: 2363-2373 (2008).

* cited by examiner

ENZYME ELECTRODE AND BIOSENSOR USING THE SAME

TECHNICAL FIELD

The present invention relates to an enzyme electrode in which an enzyme is immobilized on the electrode surface, and an electrochemical biosensor for measurement of glucose using the same.

BACKGROUND ART

An enzyme electrode used for a biosensor has a structure in which electrons generated by an enzyme reaction are received by the electrode, and the enzyme electrode may comprise an electrode and a detection layer in which enzymes and conductive particles are immobilized on the surface of the electrode using a crosslinking agent or a binder. Patent Literature 1 describes an enzyme electrode comprising an electrode and a detection layer, wherein the detection layer has an enzyme, conductive particles, and a polymer that forms an amide or ester bond with at least one of the enzyme and the conductive particle.

On the other hand, Non-patent Literature 1 has disclosed a method of using a molecule that forms a self assembled monolayer (SAM) to efficiently transfer electrons between an enzyme and a current collector (electrode). In a specific illustration in the Non-patent Literature 1, an enzyme, such as HRP (Horseraddish Peroxydase), was immobilized on the surface of the current collector via a SAM-forming molecule. However, regarding the method to immobilize enzymes via SAM-forming molecules by adsorption or the like, there has been no report of successful immobilization of glucose dehydrogenase which is one of the most used enzymes for glucose measurement biosensors. The reason may be that the catalytic site of glucose dehydrogenase is located at the center of the enzyme and thus electron transfer to the current collector is hardly occurred even when the enzyme is fixed in the vicinity of the electrode; and in particular, in the immobilization of the enzyme by random adsorption or the like, the distance between the current collector and the enzyme can not be controlled.

PRIOR ART REFERENCES

Patent Literature

Patent Literature 1: Japanese Laid-open Patent Application (Kokai) No. 2014-6154

Non-Patent Literature

Non-patent Literature 1: J. Braz. Chem. Soc. Vol. 14, No. 2, 230-243, 2003

SUMMARY OF THE INVENTION

In the method described in Patent Literature 1, a macromolecular polymer containing an oxazoline group is used as a binder. Since the distance between the enzyme and the current collector (electrode) is not controlled and varies depending on individual enzymes, there is a problem that the response value actually obtained is smaller than the response value expected from the fixed enzyme amount. Therefore, the present invention may provide an enzyme electrode for measuring glucose concentration, in which the distance between the enzyme and the current collector is controlled, and the glucose concentration may be quantitatively measured with high sensitivity In accordance with some embodiments, the present invention provides an enzyme electrode comprising;
  an electrode comprising a current collector;
  a monolayer-forming molecule bound to the surface of the current collector; and
  glucose dehydrogenase comprising a cytochrome C subunit bound to the monolayer-forming molecule;
  wherein electrons are transferred between the glucose dehydrogenase and the current collector by oxidation-reduction reaction of the glucose dehydrogenase. The monolayer may be a film formed by arrangement of molecules in one layer; the glucose dehydrogenase comprising a cytochrome C subunit may be an oligomeric enzyme comprising at least a catalytic subunit and a subunit containing cytochrome as an electron-transferring subunit; the catalytic subunit may be a subunit configured to catalyze a substrate reaction; and the electron-transferring subunit may be a subunit configured to transfer electrons to an electron acceptor. The enzyme electrode is a "direct electron transfer-type enzyme electrode" in which electrons are transferred between the enzyme and the electrode in such a way that electrons generated by an enzyme reaction are directly transferred to the electrode without the involvement of an oxidation-reduction substance, for example, including an electron transfer mediator.

In another aspect, the present invention also provides a biosensor comprising the enzyme electrode.

In another aspect, the present invention also provides a measuring apparatus comprising:
  the biosensor;
  a control section configured to control the application of voltage to the biosensor;
  a detection section configured to detect a charge transfer controlled current based on the transfer of electrons derived from a substrate to the electrode, wherein the charge transfer controlled current is obtained by the application of voltage to the biosensor;
  an arithmetic section configured to calculate the concentration of the substrate based on the current value; and
  an output section configured to output the calculated concentration of the substrate.

According to one aspect of the present invention, an enzyme may be immobilized to a current collector via a monolayer-forming molecule of controlled length by covalent bond between a reactive group of the monolayer-forming molecule and a specific amino acid residue of the enzyme. Therefore, the amount of enzyme to be immobilized in the part close to the active center of the enzyme relatively increases. This provides an enzyme electrode whose distance between the enzyme and the current collector is more controlled than immobilization of the enzyme by random adsorption. Therefore, the electron transfer efficiency between the enzyme and the current collector is improved, the response current value of the enzyme electrode may be improved, and the glucose concentration may be quantitatively measured with high sensitivity. The above-described effect is particularly remarkable for glucose dehydrogenase containing cytochrome C subunit, in which the catalytic site is located at the enzyme center.

EMBODIMENTS FOR CARRYING OUT THE INVENTION

The enzyme electrode as one embodiment of the present invention will now be described with reference to the drawings. The embodiments to be described below are provided for illustration purposes, and the present invention is not limited to the constitution of the following embodiments.

(Structure of Enzyme Electrode)

Figure 1:
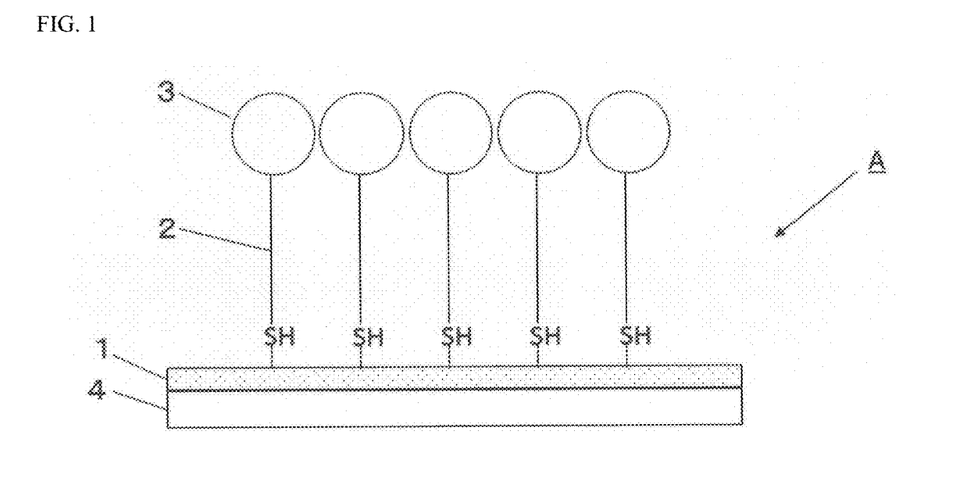
FIG. 1 is a schematic diagram illustrating an exemplary structure of an enzyme electrode according to one embodiment of the present invention.

FIG. 1 is a schematic diagram of the enzyme electrode according to some embodiments of the present invention. In FIG. 1, the enzyme electrode A comprises an insulating base plate 4, an electrode (collector) 1, and enzymes (glucose dehydrogenase comprising cytochrome C subunit) 3 immobilized on the surface (upper surface in FIG. 1) of the electrode 1 via monolayer-forming molecule 2. However, the insulating base plate 4 is not indispensable.

(Electrode)

The electrode 1 is made of a metallic material such as gold (Au), platinum (Pt), silver (Ag) and palladium (Pd), or a carbon material represented by carbons such as graphite, carbon nanotube, graphene, and mesoporous carbon, which is a current collector. The electrode 1 is formed, for example, on an insulating base plate 4 as shown in FIG. 1. The insulating base plate 4 is made of an insulating material, and examples thereof include various types of resins (plastics), such as thermoplastic resins, for example, polyetherimide (PEI), polyethylene terephthalate (PET) and polyethylene (PE), polyimide resins, and epoxy resins; glasses; ceramics; papers; and the like. The size and the thickness of the electrode 1 and the insulating base plate 4 may be selected as appropriate.

(Measurement Current)

The enzyme electrode according to some embodiments of the present invention is used to measure a charge transfer controlled current based on the transfer of electrons derived from the substance to be measured (substrate) to the electrode, rather than a current depending on the substance diffusion (diffusion controlled current). The charge transfer controlled current is a current which is generated when the electrons are transferred from the enzyme to the electrode due to the reaction between the enzyme and the substance to be measured.

In order to measure the charge transfer controlled current based on the transfer of electrons derived from a substance to be measured to an electrode, a "direct electron transfer-type enzyme electrode" may be used as a working electrode. The "direct electron transfer-type enzyme electrode" as used herein refers to a type of an enzyme electrode in which electrons are transferred between the enzyme and the electrode in such a way that electrons generated by an enzyme reaction in a reagent layer are directly transferred to the electrode without the involvement of an oxidation-reduction substance, such as an electron transfer mediator.

As shown in FIG. 1, since the enzyme 3 molecules are immobilized on the electrode 1 via the monolayer-forming molecule 2, electrons generated by the enzymatic reaction may directly move to the electrode 1. In other words, in the enzyme electrode A according to some embodiments of the present invention, electrons are transferred between the enzyme 3 and the electrode 1 due to the direct electron transfer.

(Monolayer-forming Molecule)

The monolayer-forming molecule is a compound that may bind to the current collector and may bond to the enzyme molecule, and is a compound that may form a monolayer via more than one bond to the surface of the current collector in a certain direction. The monolayer-forming molecule may have a first functional group having an affinity for the current collector, a spacer portion, and a second functional group that may react with the functional group of the enzyme molecule. The monolayer-forming molecule may have a structure in which the first functional group having an affinity for the current collector is bound to the first end of the spacer portion and the second functional group that may react with the functional group of the enzyme molecule is bound to the second end of the spacer portion.

The first functional group having affinity for the current collector is appropriately selected depending on the type of collector. The binding mode of the monolayer-forming molecule to the surface of the current collector may include one or more types of chemical bonds, for example, including covalent bond, coordinate bond or ionic bond, and/or physical bond by van der Waals force or the like. Examples of the first functional group that may bind to the current collector include thiol group and dithiol group in the case where the current collector is a metal. On the other hand, when the current collector is a carbon, pyrene and porphyrin may be exemplified as the first functional group.

The second functional group capable of reacting with the functional group of the enzyme molecule is appropriately selected depending on the type of the functional group of the enzyme molecule. An example of the second functional group when reacting with an amino group of the enzyme molecule (including a terminal amino group and a side chain amino group) includes succinimide group. In this case, the second end of the monolayer-forming molecule is a reaction residue between the succinimide group and the amino group. On the other hand, an example of the second functional group when reacting with a carboxyl group of the enzyme molecule (including a terminal carboxyl group and a side chain carboxyl group) includes oxazoline group. In this case, the second end of the monolayer-forming molecule is a reaction residue between the oxazoline group and the carboxyl group. Thus, by the reaction between the enzyme and the second functional group, the enzyme may be bound to the monolayer-forming molecule by covalent bond.

In order for the enzyme electrode to be a "direct electron transfer type enzyme electrode", the length of spacer may be a length that may keep the distance between an enzyme molecule from the electrode (current collector) surface within a certain distance. The limit distance within which the direct electron transfer could occur in a physiological reaction system is said to be from 10 to 20 Å. In the electron transfer in an electrochemical reaction system comprising an electrode and an enzyme, as well, the detection of the electron transfer on the electrode will be difficult, if the distance between the electrode and the enzyme is longer than the above mentioned limit distance, unless it involves the transfer (for example, transfer by diffusion) of a mediator. Thus, the length may be a length that may keep the distance between an enzyme and the electrode within 20 Å, and may be a length that may keep the distance between an enzyme and the electrode within 10 Å. Examples of the spacer include C1-20 (for example, C1-10 or C1-5) alkylene, C1-20 (for example, C1-10 or C1-5) alkenylene, C1-20 (for example, C1-10 or C1-5) alkynylene, a polyethylene glycol with a degree of polymerization of 2 to 50 (for example, 2 to 10, or 2 to 5), an oligopeptide having 1 to 20 amino acid residues (for example, 1 to 10, or 1 to 5). In the alkylene, alkenylene and alkynylene, one or more —CH$_2$— may be replaced by —S—, and one or more inconsecutive —CH$_2$— may be replaced by —O—.

Examples of the monolayer-forming molecule having, for example, thiol group or dithiol group include compounds having the following structure. These are SAM-forming compounds. L is a spacer, and X is an functional group which may react with a functional group of an enzyme molecule.

SH-L-X (1)

X-L-S-S-L-X (2)

Examples of such compounds include the following DSH.

Dithiobis(succinimidyl hexanoate): DSH

DSO (Dithiobis(succinimidyl octanoate)), and DSU (Dithiobis(succinimidyl undecanoate)) shown in Table 1 may also be used.

In the case of using such a monolayer-forming molecule having dithiol, two enzyme molecules may be bound per one molecule.

Examples of the monolayer-forming molecule having, for example, pyrene or porphyrin include compounds having the following structure. Py is pyrene, Po is porphyrin, L is a spacer, and X is an functional group which may react with a functional group of an enzyme molecule.

Py-L-X (3)

Po-L-X (3')

Examples of the monolayer-forming molecule having, for example, pyrene include compounds having the following structure.

1-pyrenebutanoic acid succinimidyl ester: PySE

J. Am. Chem. Soc. 2001, 123, 3838-3839, Noncovalent Sidewall Functionalization of Single-Walled Carbon Nanotubes for Protein J. Electroanal. Chem., 1994, 365, 157-164, Application of bifunctional reagents for immobilization of proteins on a carbon electrode surface: Oriented immobilization of photosynthetic reaction centers Examples of a molecule which has a pyrene and forms SAM include the following compound. The terminal of exemplified PHT is SH, which allows for, for example, addition of succinimide group to the SH group by N-(6-maleimidecaproyloxy) succinimide or the like and subsequent reaction with amino group of enzyme, or binding of an enzyme to PHT via maleimide group which is introduced to the enzyme.

PHT 17-(1-pyrenyl)-13-oxo-heptadecanethiol: PHT
Chemical Physics Letters 367 (2003) 747-752
Self-assembly of gold nanoparticles to carbon nanotubes using a thiol-terminated pyrene as interlinker (Enzyme)

As the enzyme 3, glucose dehydrogenase (GDH) comprising a cytochrome C subunit is used. The GDH including a cytochrome C subunit may be an oligomeric enzyme including at least a catalytic subunit and a subunit containing cytochrome as an electron-transferring subunit. The catalytic subunit is a subunit having a function to catalyze a substrate reaction, and the electron-transferring subunit is a subunit having a function to transfer electrons to an electron acceptor. The catalytic subunit and the catalytic domain of the GDH may contain at least one of pyrroloquinoline quinone (PQQ) and flavin adenine dinucleotide (FAD).

Examples of the GDH containing PQQ include PQQ glucose dehydrogenase (PQQGDH). Examples of the GDH containing FAD include cytochrome glucose dehydrogenase having an a subunit containing FAD. As the PQQ Glucose dehydrogenase (PQQGDH), for example, glucose-3-dehydrogenase derived from *agrobacterium tumefasience* (G3DH from *Agrobacterium tumefasience*) or a fusion protein of PQQGDH and cytochrome may be used. The fusion protein of PQQGDH and cytochrome is disclosed in WO2005/030807, for example. Examples of the GDH containing FAD include FAD-dependent glucose dehydrogenase derived from *Burkholderia cepacia* or a variant thereof. Examples of the variant of FAD-dependent glucose dehydrogenase derived from *Burkholderia cepacia* include a variant in which amino acid residues at positions 472 and 475 are substituted (WO2005/103248), a variant in which amino acid residues at positions 326, 365 and 472 are substituted (JP 2012-090563), and a variant in which amino acid residues at positions such as 365, and 326, 472, 475, and 529 are substituted (WO2006/137283).

Further, the surface of the detection layer containing an enzyme may be covered with an outer-layer film made of cellulose acetate and the like. Examples of raw materials for the outer-layer film, in addition to cellulose acetate, include: polyurethane, polycarbonate, polymethyl methacrylate, butyl methacrylate, polypropylene, polyether ether ketone, and the like.

(Method for Preparing Enzyme Electrode)

The above mentioned enzyme electrode A is prepared, for example, as follows. Specifically, a metal layer which functions as the electrode 1 is formed on one surface of the insulating base plate 4. For example, a metal layer having a desired thickness (for example, about 30 nm) is formed by depositing a metallic material, by physical vapor deposition (PVD, for example, sputtering) or chemical vapor deposition (CVD), on one surface of the insulating base plate 4 in the form of a film having a predetermined thickness (for example, about 100 μm). It is also possible to form an electrode layer made of a carbon material, instead of the metal layer. Next, monolayer-forming molecule 2 is allowed to bind onto the electrode 1. Finally, the reactive functional group of the monolayer-forming molecule and the amino group or carboxyl group of the enzyme 3 are allowed to react, which may lead to immobilization of the enzyme 3 onto the electrode 1 via the monolayer-forming molecule.

By using the enzyme electrode according to some embodiments of the present invention, the concentration of the substance to be measured (glucose) contained in a sample may be measured based on the charge transfer controlled current. The sample is not particularly limited as long as it contains the substance to be measured. However, a biological sample, for example, including blood or urine, may be used.

(Biosensor)

The enzyme electrode according to some embodiments of the present invention may be used in a biosensor as a glucose sensor. The biosensor includes, along with the enzyme electrode in accordance with some embodiments of the present invention, an electrode which serves as a counter electrode. As the counter electrode, it is possible to use any electrode which may be generally used as the counter electrode in a biosensor. Examples thereof include: a carbon electrode prepared in the form of a film by screen printing; a metal electrode prepared in the form of a film by physical vapor deposition (PVD, for example, sputtering) or chemical vapor deposition (CVD); and a silver/silver chloride electrode prepared in the form of a film by screen printing. It is also possible to employ a 3-electrode system in which the silver/silver chloride electrode or the carbon electrode prepared in the form of a film by screen printing, or the metal electrode prepared in the form of a film by physical vapor deposition (PVD, for example, sputtering) or chemical vapor deposition (CVD), is used as a reference electrode.

(Apparatus)

Figure 2:
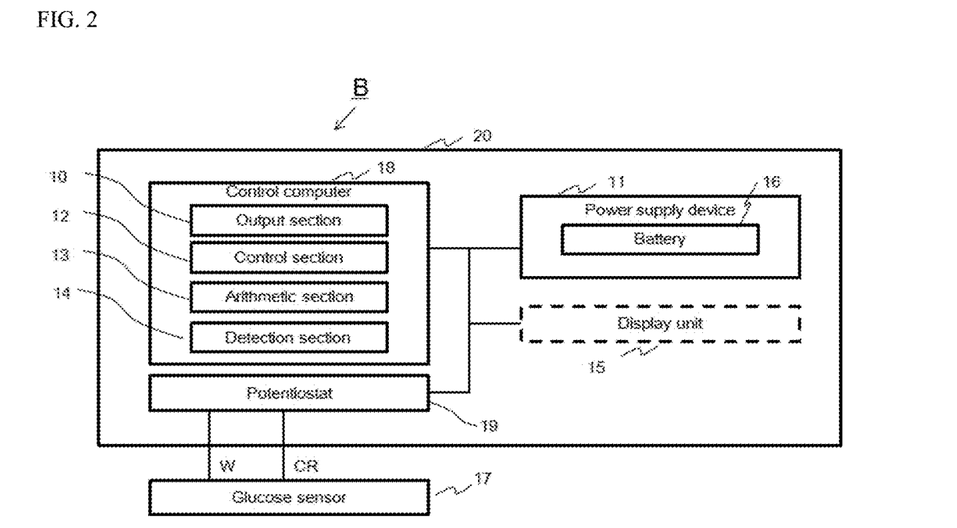
FIG. 2 is a schematic diagram illustrating one aspect of a measuring apparatus according to some embodiments of the present invention.

Next, the measuring apparatus according to some embodiments of the present invention will be described with reference to the drawings. Although one aspect of a glucose measuring apparatus is illustrated in this embodiment, the measuring apparatus according to some embodiments of the present invention is not limited to the following aspects. FIG. 2 shows an example of the configuration of main electronic components included in a measuring apparatus B. A control computer 18, a potentiostat 19 and a power supply device 11 are provided on a base plate 20 housed in a housing. The control computer 18 include, as hardware, a processor such as CPU (central processing unit); a recording medium such as a memory (RAM (Random Access Memory) or ROM (Read Only Memory)); and a communication unit. When the processor loads a program stored in the recording medium (for example, the ROM) to the RAM, and executes the program, the control computer 18 functions as an apparatus including an output section 10, a control section 12, an arithmetic section 13 and a detection section 14. The control computer 18 may also include an auxiliary memory such as a semiconductor memory (EEPROM or flash memory) or a hard disk.

The control section 12 controls the timing for applying the voltage and the value of the voltage to be applied. The power supply device 11 includes a battery 16, and supplies electricity to the control computer 18 and the potentiostat 19 for operation. It is also possible to dispose the power supply device 11 outside the housing. The potentiostat 19 is a device which maintains the potential of the working electrode constant with respect to the potential of the reference electrode. The potentiostat 19, which is controlled by the control section 12, applies a predetermined amount of voltage between the counter electrode and the working electrode of the glucose sensor 17 using terminals CR and W; measures the response current of the working electrode which may be obtained at the terminal W; and sends the result of the measurement to the detection section 14.

The arithmetic section 13 calculates the concentration of the substance to be measured based on the value of the detected current, and stores the calculated result. The output section 10 carries out data communication between the output section 10 and the display section unit 15, and sends the calculated result of the concentration of the substance to be measured provided by the arithmetic section 13 to the display section unit 15. The display section unit 15 is capable of displaying, for example, the calculated result of the glucose concentration which is received from the measuring apparatus B, on a display screen in a predetermined format.

Figure 3:
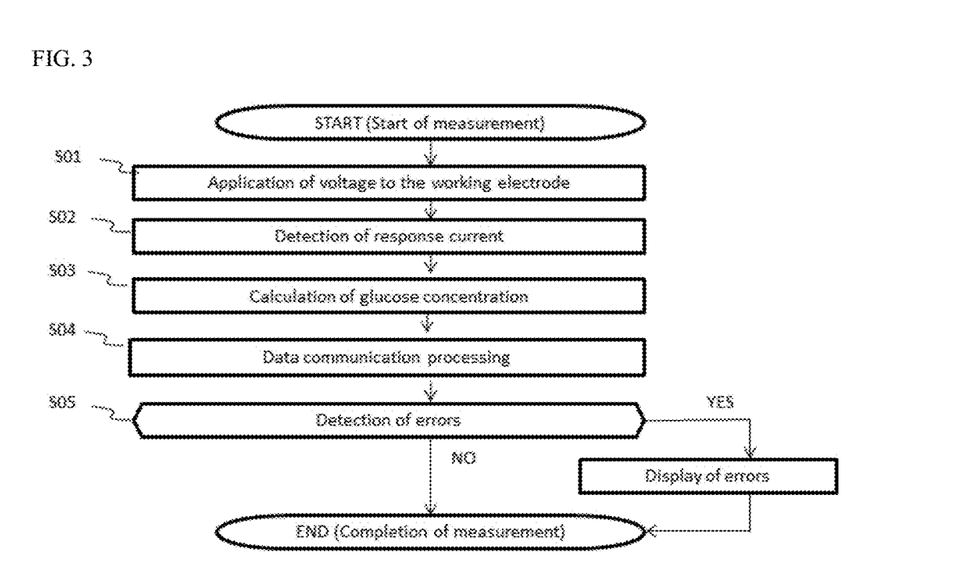
FIG. 3 is a flow chart illustrating one aspect of a measurement program using the measuring apparatus according to some embodiments of the present invention.

FIG. 3 is a flow chart showing an example of the processing sequence of the glucose concentration measurement carried out by the control computer 18. When the CPU (control section 12) of the control computer 18 receives an instruction to start the measurement of the glucose concentration, the control section 12 controls the potentiostat 19 to apply a predetermined amount of voltage (e.g., +100 to 500 mV, +100 to 400 mV or +100 to 200 mV with respect to silver/silver chloride electrode) to the working electrode, and starts measuring the response current from the working electrode (Step S01). Further, the detection of the installation of a sensor to the measuring apparatus may be used as the instruction to start the measurement of the concentration.

Next, the potentiostat 19 measures the response current obtained by the application of voltage, specifically, the charge transfer controlled current based on the transfer of electrons derived from the substance to be measured (glucose) in the sample to the electrode, for example, the steady-state current observed 1 to 20 seconds after the application of voltage. Then the potentiostat 19 sends the measured current to the detection section 14 (Step S02).

The arithmetic section 13 carries out arithmetic processing based on the measured current value, and calculates the glucose concentration (Step S03). For example, the formulae for calculating the glucose concentration or the data of the calibration curve of the glucose concentration, which correspond to the glucose dehydrogenase disposed on the electrode, are preinstalled to the arithmetic section 13 in the control computer 3, and the arithmetic section 13 calculates the glucose concentration utilizing these calculation formulae or the calibration curve.

The output section 10 sends the calculated result of the glucose concentration to the display section unit 15, through a communication link provided between the output section 10 and the display section unit 15 (Step S04). Thereafter, the control section 12 determines if there are any measurement errors detected (Step S05); completes the measurement if there is no error; and displays the glucose concentration on the display section. If there are any errors, a notification of error is displayed, and then the flow sequence shown in FIG. 3 is completed. Further, the calculated result may be stored in the arithmetic section 13, so that the stored result may be reloaded afterwards to be displayed on the display section for confirmation. Although the detection of measurement errors by the control section 12 (Step S05) is carried out after the calculated result is sent to the display section unit 15 (Step S04) in this embodiment, it is also possible to carry out these steps in different orders.

EXAMPLES

Examples of the enzyme electrode are described below. However, the present invention is not limited to the aspects of the following Examples.

Example 1

(Preparation of Enzyme Electrode)

An enzyme electrode was prepared by immobilizing GDH containing cytochrome C subunit on the gold surface via a monolayer-forming molecule. As the monolayer-forming molecule, the following DSH was used.

Dithiobis(succinimidyl hexanoate): DSH

Specifically, a gold wire (3 mm in tip) was immersed in a Piranha solution (200 µl) at room temperature overnight, then washed with acetone, immersed in a DSH solution in acetone (concentration 1 µM, 10 µM or 90 µM) and incubated at 25° C. for 8 hours to allow thiol group of DSH to bind to the gold surface. Subsequently, it was washed with acetone, immersed in HEPES (100 µl) containing an enzyme (FADGDH derived from *Burkholderia cepacia* (concentration 0.028 mg/ml)) and incubated at 4° C. for 2 hours to allow the enzyme to bind via a functional group of DSH to obtain an enzyme electrode.

(Measurement of Glucose Concentration)

The response current value for 0 mM (background), 1 mM, 3 mM, 5 mM, 10 mM, 15 mM, or 20 mM aqueous solution of glucose was measured using the enzyme electrode (2 lots for each adjusted with DSH concentration of 1 µM, 10 µM, 90 µM) by chronoamperometry. The glucose measurement was carried out at 37° C. using counter electrode (Pt wire), reference electrode (silver/silver chloride), with a voltage of +0.4 V applied to the working electrode (vs. silver/silver chloride).

(Evaluation of Measurement Results)

Figure 4:
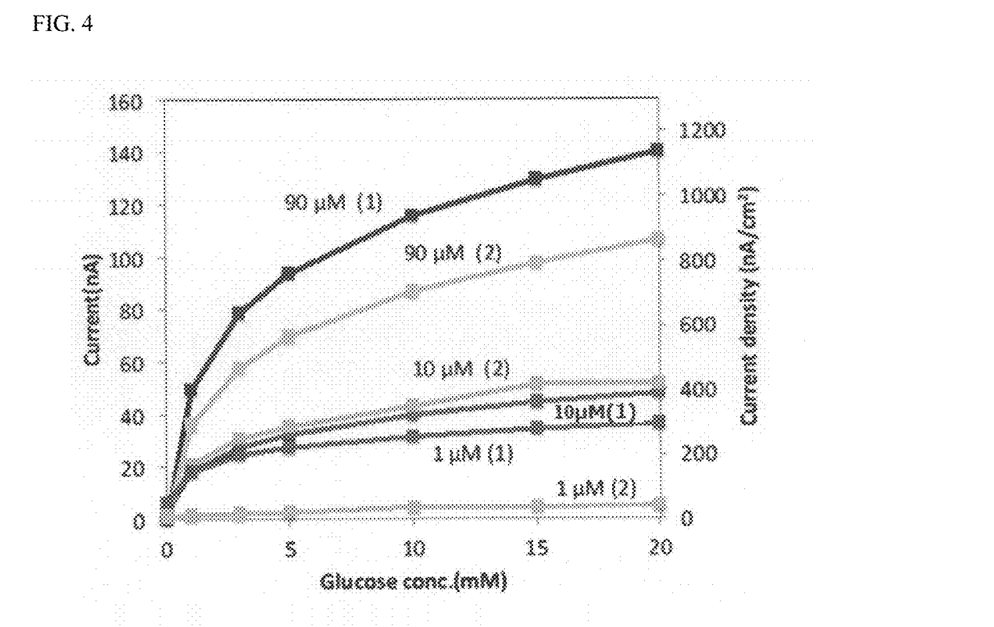
FIG. 4 is a graph showing the relationship between glucose concentration and response current when the enzyme electrode (electrode material: gold) according to one aspect of the present invention on which an enzyme is immobilized using DSH as a monolayer-forming molecule is used.

The results are shown in FIG. 4. According to the test results shown in FIG. 4, when the concentration of monolayer-forming molecule (DSH) was 1 µM, the S/B ratio was low and reproducibility was not sufficient, but when the concentration was 10 µM, reproducibility and S/B ratio suitable for measuring glucose concentration were obtained.

Example 2

(Preparation of Enzyme Electrode)

In order to confirm the difference in direct electron transfer efficiency due to the presence or absence of monolayer-forming molecule, the responses of the electrode prepared without monolayer-forming molecule and the electrode prepared with monolayer-forming molecule were compared. Specifically, for the electrode without the monolayer-forming molecule, a gold wire (3 mm in tip) was immersed in a Piranha solution (200 µl) at room temperature overnight, then washed with acetone, immersed in HEPES (100 µl) containing an enzyme (FADGDH derived from *Burkholderia cepacia* (concentration 0.028 mg/ml)), and incubated at 4° C. for 2 hours to allow the enzyme to be adsorbed onto the gold surface to obtain an enzyme electrode. For the electrode with the monolayer-forming molecule, the electrode was prepared in the same process as the above-described process except that after washing with acetone after the treatment with a Piranha solution, the resultant electrode was immersed in an DSH solution in acetone (concentration 10 µM) and incubated at 25° C. for 24 hours to allow the thiol group of DSH to bind to the gold surface.

(Measurement of Glucose Concentration)

The response current value for 0 mM (background), 1 mM, 3 mM, 5 mM, 10 mM, 15 mM, or 20 mM aqueous solution of glucose was measured using the enzyme electrode (2 lots for each prepared with and without DSH) by chronoamperometry. The glucose measurement was carried out at 37° C. using counter electrode (Pt wire), reference electrode (silver/silver chloride), with a voltage of +0.4 V applied to the working electrode (vs. silver/silver chloride).

(Evaluation of Measurement Results)

Figure 5:
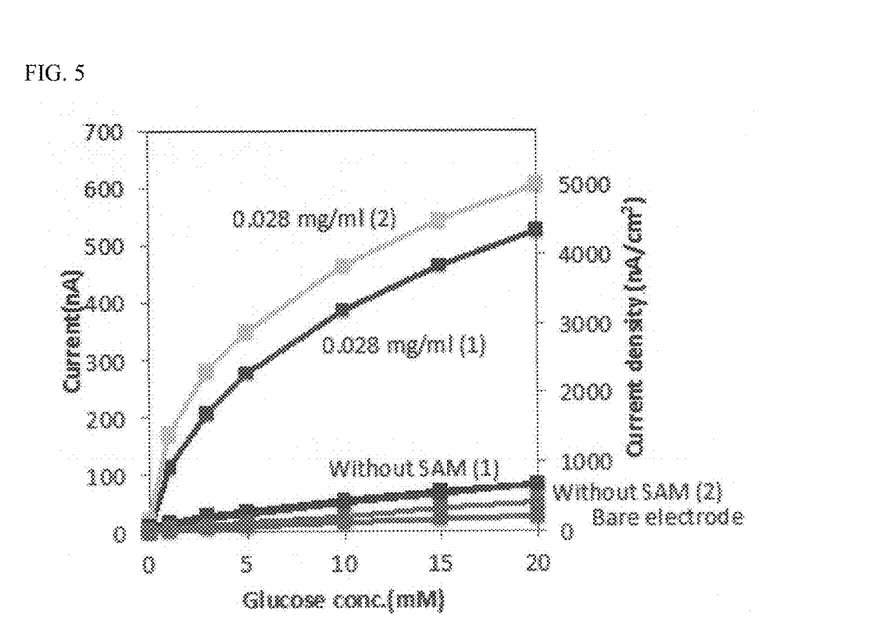
FIG. 5 is a graph showing the relationship between glucose concentration and response current when the enzyme electrode (electrode material: gold) according to one aspect of the present invention on which an enzyme is immobilized using DSH as a monolayer-forming molecule or the enzyme electrode (electrode material: gold) on which an enzyme is directly adsorbed without DSH is used (+400 mV). The Bare electrode is a measurement result of an electrode on which an enzyme is adsorbed on an electrode not subjected to a Piranha treatment.

The results are shown in FIG. 5. According to the test results shown in FIG. 5, when the enzyme was immobilized via a monolayer-forming molecule (DSH), a current value by glucose concentration measurement was 7.5 times than that without DSH.

Example 3

(Preparation of Enzyme Electrode)

In order to confirm the difference in direct electron transfer efficiency due to the spacer length of the monolayer, an enzyme electrode on which GDH containing cytochrome C subunit was immobilized on the gold surface via each monolayer-forming molecule was prepared. As the monolayer-forming molecule, the following DSH, DSO (Dithiobis(succinimidyl octanoate)) or DSU (Dithiobis(succinimidyl undecanoate)) was used.

TABLE 1

| Name of Compound | Structural Formula | 2 X spacer length (Å) |
|---|---|---|
| Dithiobis(succinimidyl hexanoate) | 16.6-17.6Å | 16.6-17.6 |

TABLE 1-continued

| Name of Compound | Structural Formula | 2 X spacer length (Å) |
|---|---|---|
| Dithiobis(succinimidyl octanoate) | 21.8-22.8Å | 21.8-22.8 |
| Dithiobis(succinimidyl undecanoate) | 29.7-30.7Å | 29.7-30.7 |

Specifically, a gold wire (3 mm in tip) was immersed in a Piranha solution (200 μl) at room temperature overnight, then washed with acetone, immersed in each monolayer-forming molecule solution in acetone (concentration 10 μM) and incubated at 25° C. for 24 hours to allow thiol group of DSH to bind to the gold surface. Subsequently, the resultant electrode was washed with acetone, immersed in HEPES (100 μl) containing an enzyme (FADGDH derived from *Burkholderia cepacia* (concentration 0.028 mg/ml)) and incubated at 4° C. for 2 hours to allow the enzyme to bind to obtain an enzyme electrode.

(Measurement of Glucose Concentration)

The response current value for 0 mM (background), 1 mM, 3 mM, 5 mM, 10 mM, 15 mM, or 20 mM aqueous solution of glucose was measured using the enzyme electrode (3 lots for each prepared with DSH, DSO or DSU) by chronoamperometry. The glucose measurement was carried out at 37° C. using counter electrode (Pt wire), reference electrode (silver/silver chloride), with a voltage of +0.4 V applied to the working electrode (vs. silver/silver chloride). The current value when the current became steady was sampled as the measured value.

(Evaluation of Measurement Results)

Figure 6:
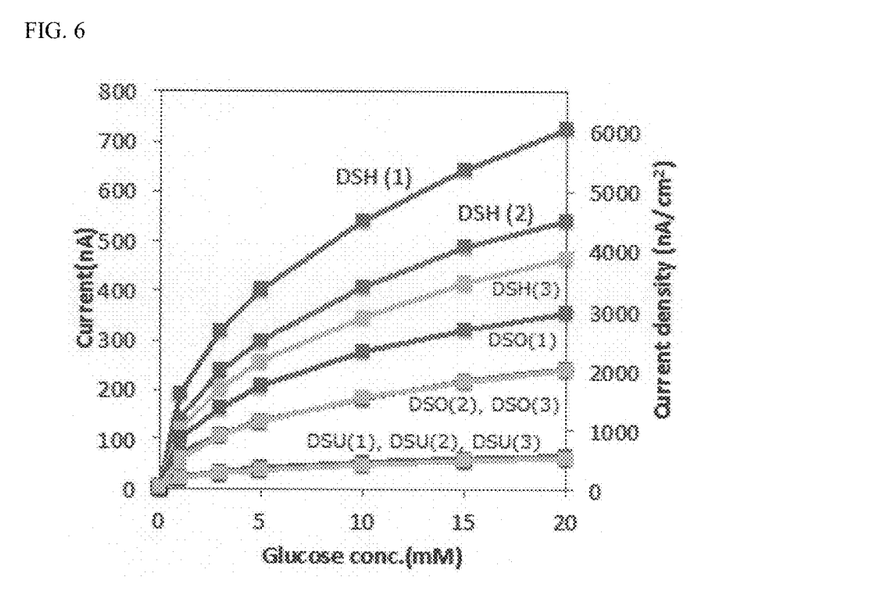
FIG. 6 is a graph showing the relationship between glucose concentration and response current when the enzyme electrode (electrode material: gold) according to one aspect of the present invention on which an enzyme is immobilized using DSH, DSO or DSU as a monolayer-forming molecule is used.

The results are shown in FIG. 6. According to the test results shown in FIG. 6, as the spacer length of the monolayer-forming molecule became shorter, a higher current value by glucose concentration measurement was obtained.

Example 4

(Analysis of the Effects of Acetaminophen (AP) and Ascorbic Acid (AA))

Figure 7A:
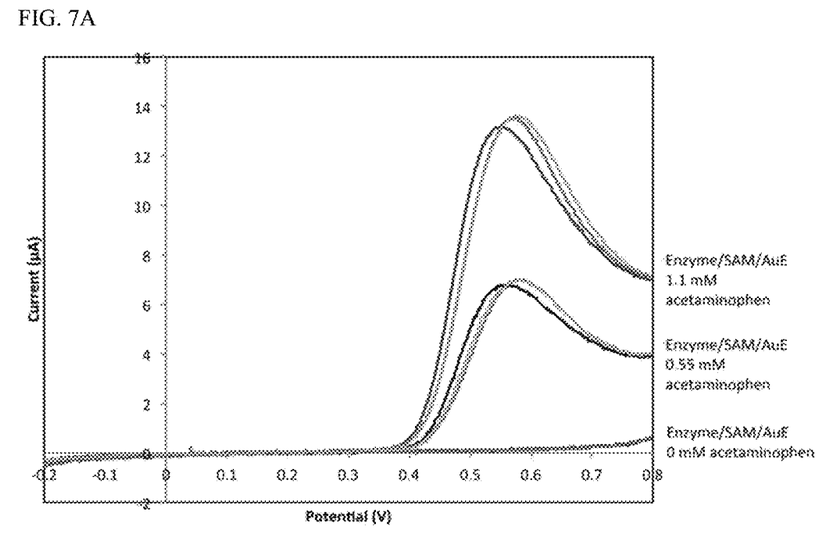
FIG. 7A is a graph showing the relationship between applied voltage and response current for the sample containing acetaminophen when the enzyme electrode (electrode material: gold) according to one aspect of the present invention on which an enzyme is immobilized using DSH as a monolayer-forming molecule is used.
Figure 7B:
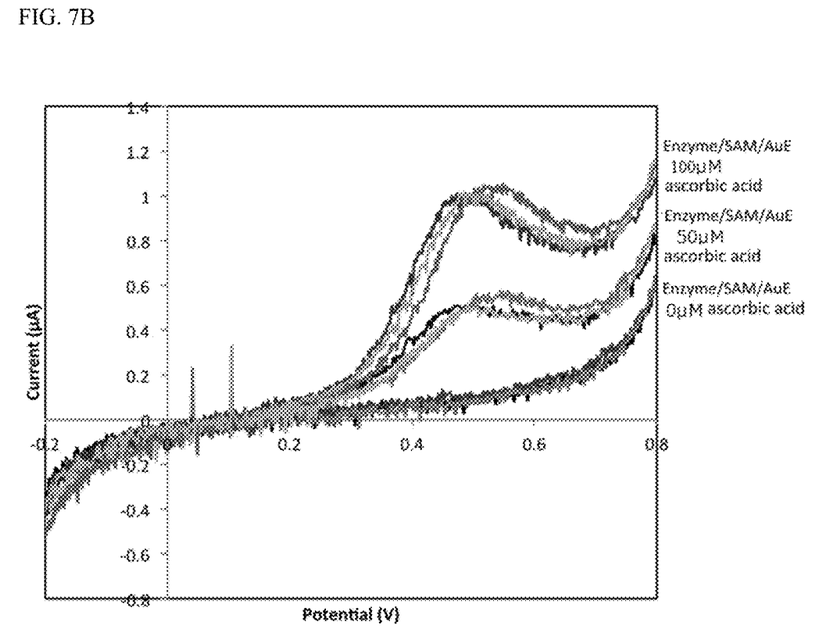
FIG. 7B is a graph showing the relationship between applied voltage and response current for the sample containing ascorbic acid (B) when the enzyme electrode (electrode material: gold) according to one aspect of the present invention on which an enzyme is immobilized using DSH as a monolayer-forming molecule is used.

Whether the electrode to which the enzyme was immobilized via the monolayer-forming molecule is affected by acetaminophen and ascorbic acid was analyzed. Using the enzyme electrode prepared in Example 2 (DSH, three lots for each experiment), the response current for acetaminophen (1.1 mM, 0.55 mM, or 0 mM) and ascorbic acid (100 μM, 50 μM, or 0 μM) was measured by linear sweep voltammetry. The glucose measurement was carried out using counter electrode (Pt wire), reference electrode (silver/silver chloride), with a voltage of −0.2 to +0.8 V applied to the working electrode (vs. silver/silver chloride). The result is shown in FIG. 7A and FIG. 7B. The current was observed when the voltage exceeded about 400 mV for acetaminophen and when the voltage exceeded about 200 mV for ascorbic acid. These results suggested that the contamination of acetaminophen and ascorbic acid may affect the measurement of glucose value.

Figure 8:
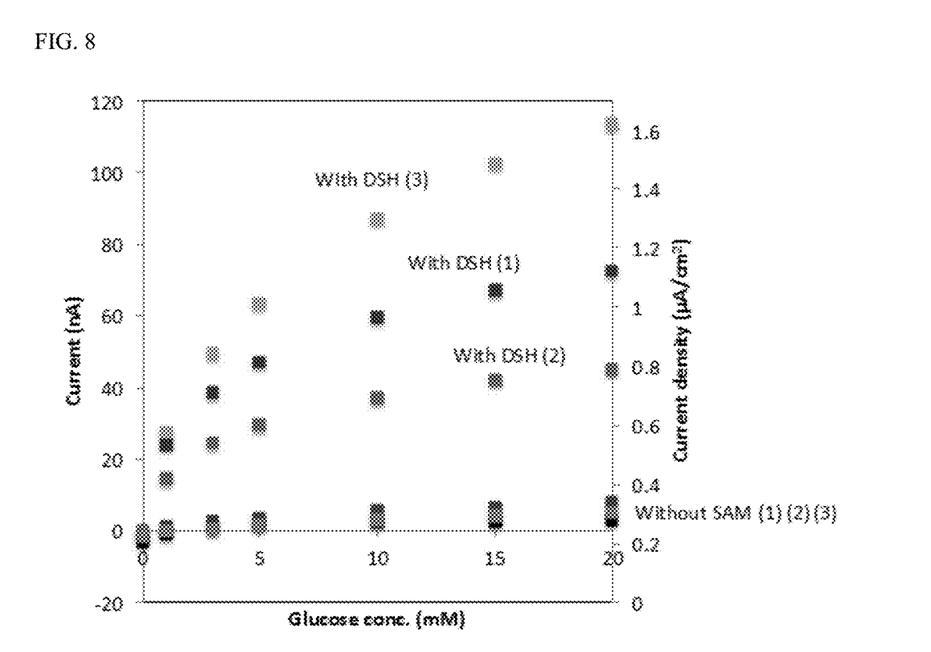
FIG. 8 is a graph showing the relationship between glucose concentration and response current when the enzyme electrode (electrode material: gold) according to one aspect of the present invention on which an enzyme is immobilized using DSH as a monolayer-forming molecule or the enzyme electrode (electrode material: gold) on which an enzyme is directly adsorbed without DSH is used (+100 mV).

From the above result, it was considered that glucose measurement should be conducted with a low voltage when the test sample for measurement may contain contaminants such as acetaminophen and ascorbic acid. Then, the same chronoamperometry experiment as Example 2 was performed with the applied voltage of +100 mV with respect to silver/silver chloride (three lots for each experiment). As a result, as shown in FIG. 8, the current was detected at the low voltage (+100 mV) for the electrode where the enzyme was immobilized via the monolayer-forming molecule (with DSH), and the current value was more than ten times higher than that for the electrode where the enzyme was directly adsorbed (without SAM).

Figure 9:
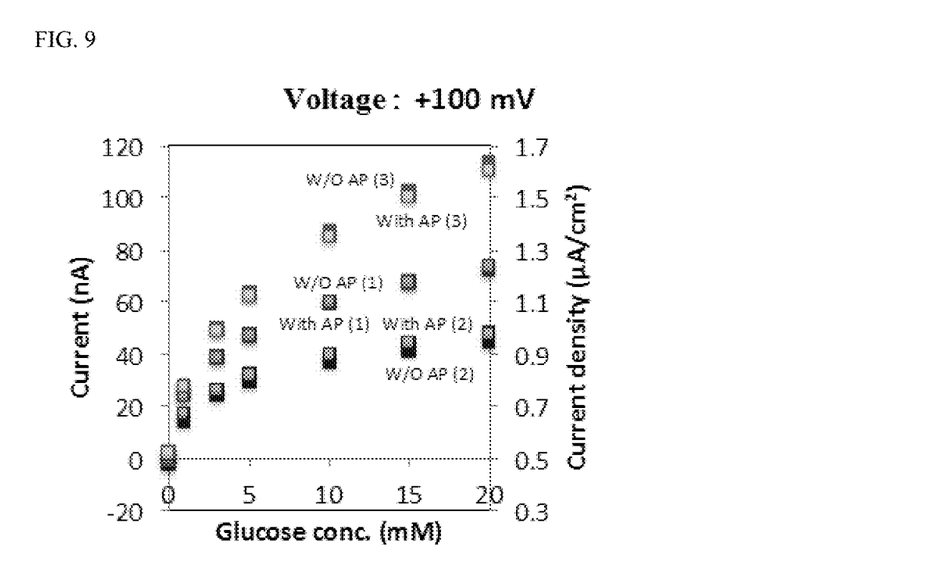
FIG. 9 is a graph showing the relationship between glucose concentration and response current in the presence or absence of acetaminophen when the enzyme electrode (electrode material: gold) according to one aspect of the present invention on which an enzyme is immobilized using DSH as a monolayer-forming molecule is used (+100 mV). The Bare electrode is a measurement result of an electrode on which an enzyme is adsorbed on an electrode not subjected to a Piranha treatment.
Figure 10:
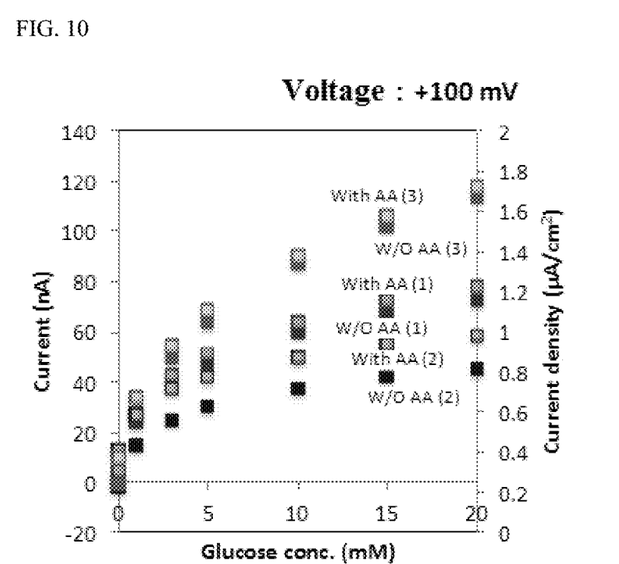
FIG. 10 is a graph showing the relationship between glucose concentration and response current in the presence or absence of ascorbic acid when the enzyme electrode (electrode material: gold) according to one aspect of the present invention on which an enzyme is immobilized using DSH as a monolayer-forming molecule is used (+100 mV). The Bare electrode is a measurement result of an electrode on which an enzyme is adsorbed on an electrode not subjected to a Piranha treatment.

Then, whether the measurement at the voltage of +100 mV is affected by ascorbic acid and acetaminophen was analyzed. The same chronoamperometry experiment as FIG. 8 was performed using the enzyme electrode (DSH) prepared in Example 2 for the glucose solution containing 100 μM ascorbic acid or 1.1 mM acetaminophen (three lots for each experiment). As a result, as shown in FIGS. 9 and 10, in the case of using the enzyme electrode where the enzyme was immobilized via the monolayer-forming molecule and applying the voltage of +100 mV, the current values observed for the glucose solution containing ascorbic acid or acetaminophen with were almost the same as that observed for the glucose solution not containing ascorbic acid or acetaminophen. The same was true for the applied voltage of +150 mV. Therefore, it was found that the enzyme electrode using the monolayer-forming molecule is less affected by ascorbic acid and acetaminophen, especially at the low voltage.

Figure 11A:
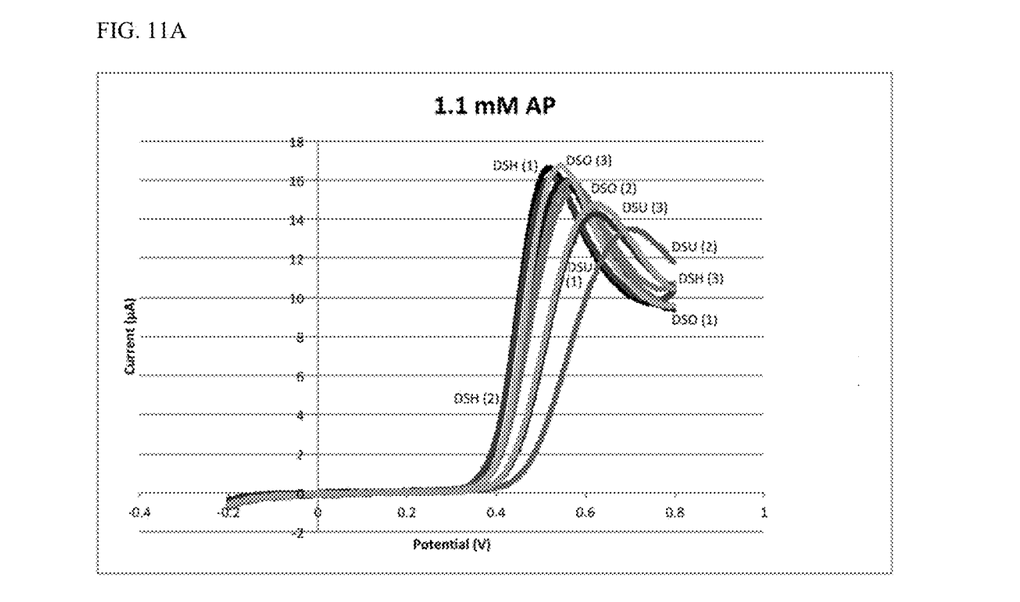
FIG. 11A is a graph showing the relationship between applied voltage and response current for the sample containing acetaminophen (A) when the enzyme electrode (electrode material: gold) according to one aspect of the present invention on which an enzyme is immobilized using DSH DSO or DSU as a monolayer-forming molecule is used.
Figure 11B:
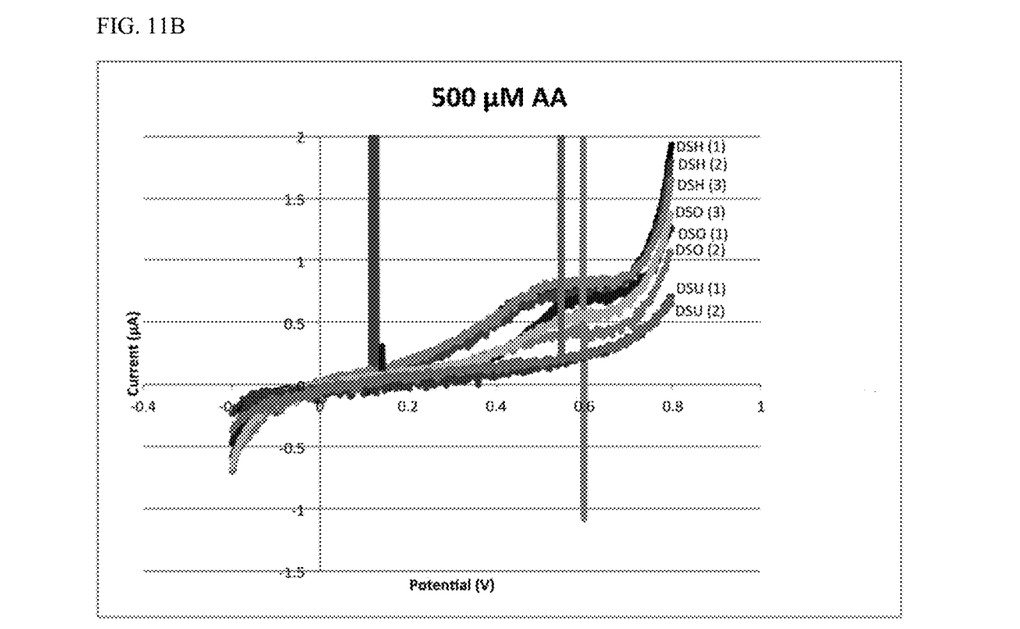
FIG. 11B is a graph showing the relationship between applied voltage and response current for the sample containing ascorbic acid (B) when the enzyme electrode (electrode material: gold) according to one aspect of the present invention on which an enzyme is immobilized using DSH DSO or DSU as a monolayer-forming molecule is used.

Using DSH, DSO, and DSU shown in Table 1, the relationship between the effects of ascorbic acid and acetaminophen and the length of linker (spacer) of the monolayer-forming molecule was analyzed by linear sweep voltammetry with a voltage of −0.2 to +0.8 V applied to the working electrode (vs. silver/silver chloride) (three or two lots for each experiment). As a result shown in FIG. 11A and FIG. 11B, the effects of ascorbic acid and acetaminophen were diminished as the length of the linker was increased at the same voltage. Therefore, it was suggested that the effects of contaminants on the electrode surface may be blocked by using a monolayer-forming molecule with a longer linker (spacer).

Example 5

(Preparation of Enzyme Electrode)

An enzyme electrode was prepared by immobilizing GDH containing cytochrome C subunit on a carbon surface via a monolayer-forming molecule. As the monolayer-forming molecule, the following PySE was used.

1-pyrenebutanoic acid succinimidyl ester: PySE

Specifically, 10 µl of PySE solution in acetone (concentration 10 µM) was added to mesoporous carbon (56 µg), incubated for 1 hour at room temperature, and allowed acetone to volatilize at room temperature for 1 hour to obtain PySE-modified mesoporous carbon powder. To this was added 3 µl of FADGDH derived from *Burkholderia cepacia* (concentration 27.7 mg/ml) and 6 µl of HEPES (pH 8.0, concentration 50 mM), incubated for 1 hour at room temperature, and then 1 µl of sucrose aqueous solution (concentration 20%) was added to obtain an enzyme-immobilized mesoporous carbon dispersion. The dispersion was added dropwise in 0.05 µl portions four times to a film-like electrode (electrode area: 0.1 mm$^2$) formed by gold sputtering. After drying, the resultant allowed to stand in a saturated steam environment of glutaraldehyde for 1 hour at room temperature to cause crosslinking, thereby fixing the enzyme/PySE modified mesoporous carbon onto the gold electrode. Thereafter, the electrode was immersed in a Tris-HCl aqueous solution (concentration 10 mM) for 20 minutes to block unreacted GA to obtain an enzyme/PySE/mesoporous carbon electrode. As a comparative control, an enzyme electrode without PySE was simultaneously prepared. Specifically, 3 µl of FADGDH derived from *Burkholderia cepacia* (concentration 27.7 mg/ml) and 6 µl of HEPES (pH 8.0, concentration 50 mM) were added to 56 µg of unmodified mesoporous carbon instead of PySE immobilized mesoporous carbon, and 1 µl of an aqueous solution of sucrose (concentration 20%) was added to obtain a mesoporous carbon dispersion in which the enzyme was adsorbed. The dispersion was added dropwise in 0.05 µl portions four times to a film-like electrode (electrode area: 0.1 mm$^2$) formed by gold sputtering. After drying, the resultant allowed to stand in a saturated steam environment of glutaraldehyde for 1 hour at room temperature to cause crosslinking, thereby fixing the enzyme/PySE modified mesoporous carbon onto the gold electrode. Thereafter, the electrode was immersed in a Tris-HCl aqueous solution (concentration 10 mM) for 20 minutes to block unreacted GA to obtain an enzyme-adsorbed mesoporous carbon electrode.

(Measurement of Glucose Concentration)

The response current value for 0 mM (background), 1 mM, 3 mM, 5 mM, 10 mM, 15 mM, or 20 mM aqueous solution of glucose was measured using the enzyme electrode (2 lots for each adjusted with DSH concentration of 1 µM, 10 µM, 90 µM) by chronoamperometry. The glucose measurement was carried out at 37° C. using counter electrode (Pt wire), reference electrode (silver/silver chloride), with a voltage of +0.4 V applied to the working electrode (vs. silver/silver chloride). The current value when the current became steady was sampled as the measured value.

(Evaluation of Measurement Results)

Figure 12:
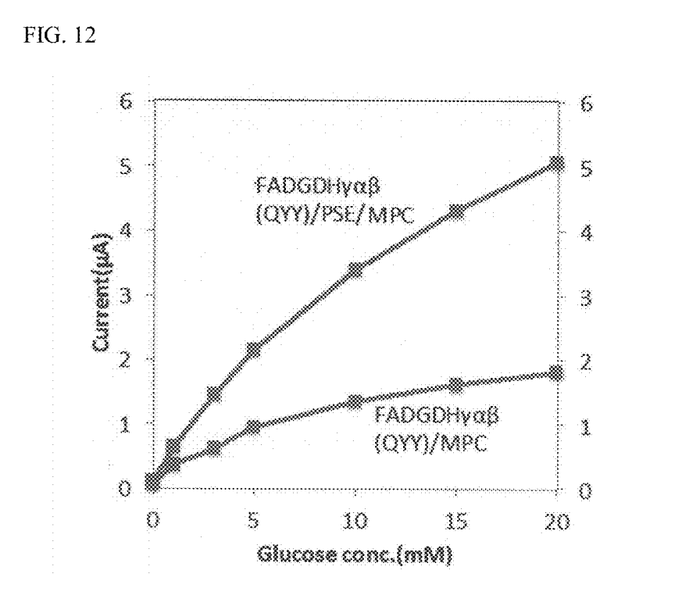
FIG. 12 is a graph showing the relationship between glucose concentration and response current when the enzyme electrode (electrode material: carbon) according to one aspect of the present invention on which an enzyme is immobilized using PySE as a monolayer-forming molecule is used.

The results are shown in FIG. 12.

According to the test results shown in FIG. 12, in the case where the enzyme was immobilized using a monolayer-forming molecule (PySE), a current value in glucose measurement higher by 2.5 times than the case where the electrode was prepared by adsorption alone was obtained.

DESCRIPTION OF SYMBOLS

A enzyme electrode
1 electrode
2 monolayer-forming molecule
3 enzyme
4 insulating base plate
B measuring apparatus
10 output section
11 power supply device
12 control section
13 arithmetic section
14 detection section
15 display section unit
16 battery
17 glucose sensor
18 control computer
19 potentiostat
20 base plate
CR, W terminal While the invention has been described in detail with reference to exemplary embodiments thereof, it will be apparent to one skilled in the art that various changes may be made, and equivalents employed, without departing from the scope of the invention. Each of the aforementioned documents as well as JP2016-102232 is incorporated by reference herein in its entirety.

What is claimed is:

1. An enzyme electrode, comprising:
   an electrode comprising a current collector;
   a monolayer-forming molecule bound to the surface of the current collector; and
   a glucose dehydrogenase comprising a cytochrome C subunit bound to the monolayer-forming molecule;
   wherein electrons are transferred between the glucose dehydrogenase and the current collector by oxidation-reduction reaction of the glucose dehydrogenase,
   the monolayer-forming molecule comprises an oxazoline group, and is bound to the glucose dehydrogenase by a reaction between the oxazoline group of the monolayer-forming molecule and the carboxyl group of the glucose dehydrogenase.

2. The enzyme electrode according to claim 1, wherein the current collector comprises a metal selected from the group consisting of gold, palladium, silver and platinum.

3. The enzyme electrode according to claim 2, wherein the monolayer-forming molecule is a molecule having a thiol group or a dithiol group.

4. The enzyme electrode according to claim 1, wherein the current collector comprises a carbon material selected from the group consisting of graphite, carbon nanotube, graphene, and mesoporous carbon.

5. The enzyme electrode according to claim 4, wherein the monolayer-forming molecule is a molecule having a pyrene.

6. The enzyme electrode according to claim 1, which is a direct electron transfer-type enzyme electrode.

7. A biosensor comprising the enzyme electrode according to claim 1.

8. The enzyme electrode according to claim 1, wherein the electrode comprises a material selected from the group consisting of gold (Au), platinum (Pt), silver (Ag), palladium (Pd), and a carbon material.

9. The enzyme electrode according to claim 1, wherein the electrode comprises gold.

10. The enzyme electrode according to claim 1, wherein the electrode is formed on an insulating base plate.

11. The enzyme electrode according to claim 10, wherein wherein the insulating base plate comprises a material selected from the group consisting of polyetherimide (PEI), polyethylene terephthalate (PET), polyethylene (PE), polyimide resins, epoxy resins, glasses, ceramics and papers.

12. The enzyme electrode according to claim 1, wherein the glucose dehydrogenase comprises an oligomeric enzyme including at least a catalytic subunit and a subunit containing cytochrome as an electron-transferring subunit.

13. The enzyme electrode according to claim 12, wherein the catalytic subunit and the catalytic domain of the glucose dehydrogenase includes at least one of pyrroloquinoline quinone (PQQ) and flavin adenine dinucleotide (FAD).

14. The enzyme electrode according to claim 1, wherein the glucose dehydrogenase comprises PQQ glucose dehydrogenase (PQQGDH) or cytochrome glucose dehydrogenase having an α subunit containing FAD.

* * * * *